United States Patent
Tang et al.

(10) Patent No.: US 10,949,951 B2
(45) Date of Patent: Mar. 16, 2021

(54) PATIENT-SPECIFIC DEEP LEARNING IMAGE DENOISING METHODS AND SYSTEMS

(71) Applicant: General Electric Company, Schenectady, NY (US)

(72) Inventors: Jie Tang, Waukesha, WI (US); Eric Gros, Waukesha, WI (US); Jiang Hsieh, Waukesha, WI (US); Roy Nilsen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 16/110,764

(22) Filed: Aug. 23, 2018

(65) Prior Publication Data

US 2020/0065940 A1 Feb. 27, 2020

(51) Int. Cl.
*G06T 5/00* (2006.01)
*G16H 30/20* (2018.01)
*G06N 20/00* (2019.01)
*G06K 9/62* (2006.01)
*G06T 3/40* (2006.01)

(52) U.S. Cl.
CPC ............ *G06T 5/002* (2013.01); *G06K 9/6256* (2013.01); *G06N 20/00* (2019.01); *G06T 3/40* (2013.01); *G16H 30/20* (2018.01); *G06T 2207/20081* (2013.01); *G06T 2207/20084* (2013.01)

(58) Field of Classification Search
CPC combination set(s) only.
See application file for complete search history.

(56) References Cited

U.S. PATENT DOCUMENTS

| | | | |
|---|---|---|---|
| 7,136,538 B2* | 11/2006 | Kitagawa | H04N 19/51 382/275 |
| 8,300,120 B2* | 10/2012 | Shohara | G06T 5/20 348/241 |
| 8,824,753 B2* | 9/2014 | Souza | G06T 5/002 382/128 |
| 10,685,429 B2* | 6/2020 | Mentl | G06T 5/002 |
| 2006/0056724 A1* | 3/2006 | Le Dinh | G06K 9/40 382/274 |
| 2018/0349759 A1* | 12/2018 | Isogawa | G06N 3/0454 |
| 2019/0098034 A1* | 3/2019 | Wakasugi | H04L 63/1425 |
| 2019/0138838 A1* | 5/2019 | Liu | G06T 3/4053 |
| 2019/0139191 A1* | 5/2019 | Liu | G06N 3/0454 |
| 2019/0164288 A1* | 5/2019 | Wang | G06T 5/005 |
| 2020/0126191 A1* | 4/2020 | Munkberg | G06T 5/50 |
| 2020/0160520 A1* | 5/2020 | Prosky | G06N 20/20 |

* cited by examiner

*Primary Examiner* — Anand P Bhatnagar

(57) ABSTRACT

Systems and methods for improved image denoising using a deep learning network model are disclosed. An example system includes an input data processor to process a first patient image of a first patient to add a first noise to the first patient image to form a noisy image input. The example system includes an image data denoiser to process the noisy image input using a first deep learning network to identify the first noise. The image data denoiser is to train the first deep learning network using the noisy image input. When the first deep learning network is trained to identify the first noise, the image data denoiser is to deploy the first deep learning network as a second deep learning network model to be applied to a second patient image of the first patient to identify a second noise in the second patient image.

17 Claims, 19 Drawing Sheets

PATIENT-SPECIFIC DEEP LEARNING IMAGE DENOISING METHODS AND SYSTEMS

FIELD OF THE DISCLOSURE

This disclosure relates generally to improved medical systems and, more particularly, to improved machine learning systems and methods for medical image processing.

BACKGROUND

Image noise is random variation in image data (e.g., variation in brightness and/or color information for an image) introduced by a component of the image acquisition process (e.g., introduced by a defect or wear in an image source, image detector, other part of an imaging scanner, error in image processing software, heating of a sensor and/or other imaging equipment, etc.). In x-ray and/or computed tomography imaging, quantum noise due to Poisson statistics of x-ray photons can be a source of noise in an image, for example. Noise or interference in an image can corrupt actual image data and/or otherwise obscure features in a resulting image. As such, noise in an image can be highly disruptive and even dangerous to a patient if noise in an image prevents a clinician (e.g., a radiologist, a specialist, a surgeon, etc.) from diagnosing a health issue or properly preparing for a procedure.

Healthcare provider tasks including image processing and analysis, etc., are time consuming and resource intensive tasks that are impractical, if not impossible, for humans to accomplish alone. The addition of noise in an image to be processed, analyzed, and relied upon for patient treatment and safety further complicates an already difficult, yet vital, task.

BRIEF DESCRIPTION

Certain examples provide systems and methods for improved image denoising using a deep learning network model.

Certain examples provide image data processing system including an input data processor, an image data denoiser, a post-processing image generator, and an output imager. The example input data processor is to process a first patient image of a first patient to add a first noise to first patient image to form a noisy image input. The example image data denoiser is to process the noisy image input using a first deep learning network to identify the first noise. The example image data denoiser is to train the first deep learning network using the noisy image input and to modify a network weight based on a comparison of a noise output of the first deep learning network to an expected noise output. When the first deep learning network is trained to identify the first noise, the image data denoiser is to deploy the first deep learning network as a second deep learning network model to be applied to a second patient image of the first patient to identify a second noise in the second patient image. The example post-processing image generator is to remove the second noise identified by the second deep learning network model from the second patient image to form a denoised patient image. The example output imager is to output the denoised patient image.

Certain examples provide a computer-readable storage medium including instructions which, when executed, cause at least one processor to at least: process a first patient image of a first patient to add a first noise to the first patient image to form a noisy image input; train the first deep learning network using the noisy image input as input to identify the first noise; and when the first deep learning network is trained to identify the first noise, deploy the first deep learning network as a second deep learning network model to be applied to a second patient image of the first patient to identify a second noise in the second patient image, wherein the second noise identified by the second deep learning network model is to be removed from the second patient image to form a denoised patient image to be output.

Certain examples provide a computer-implemented method of image denoising including: processing, using at least one processor, a first patient image of a first patient to add a first noise to the first patient image to form a noisy image input; training, using the at least one processor, the first deep learning network using the noisy image input as input to identify the first noise; and when the first deep learning network is trained to identify the first noise, deploying, using the at least one processor, the first deep learning network as a second deep learning network model to be applied to a second patient image of the first patient to identify a second noise in the second patient image, wherein the second noise identified by the second deep learning network model is to be removed from the second patient image to form a denoised patient image to be output.

BRIEF DESCRIPTION OF THE DRAWINGS

The figures are not scale. Wherever possible, the same reference numbers will be used throughout the drawings and accompanying written description to refer to the same or like parts.

DETAILED DESCRIPTION

Figure 1:
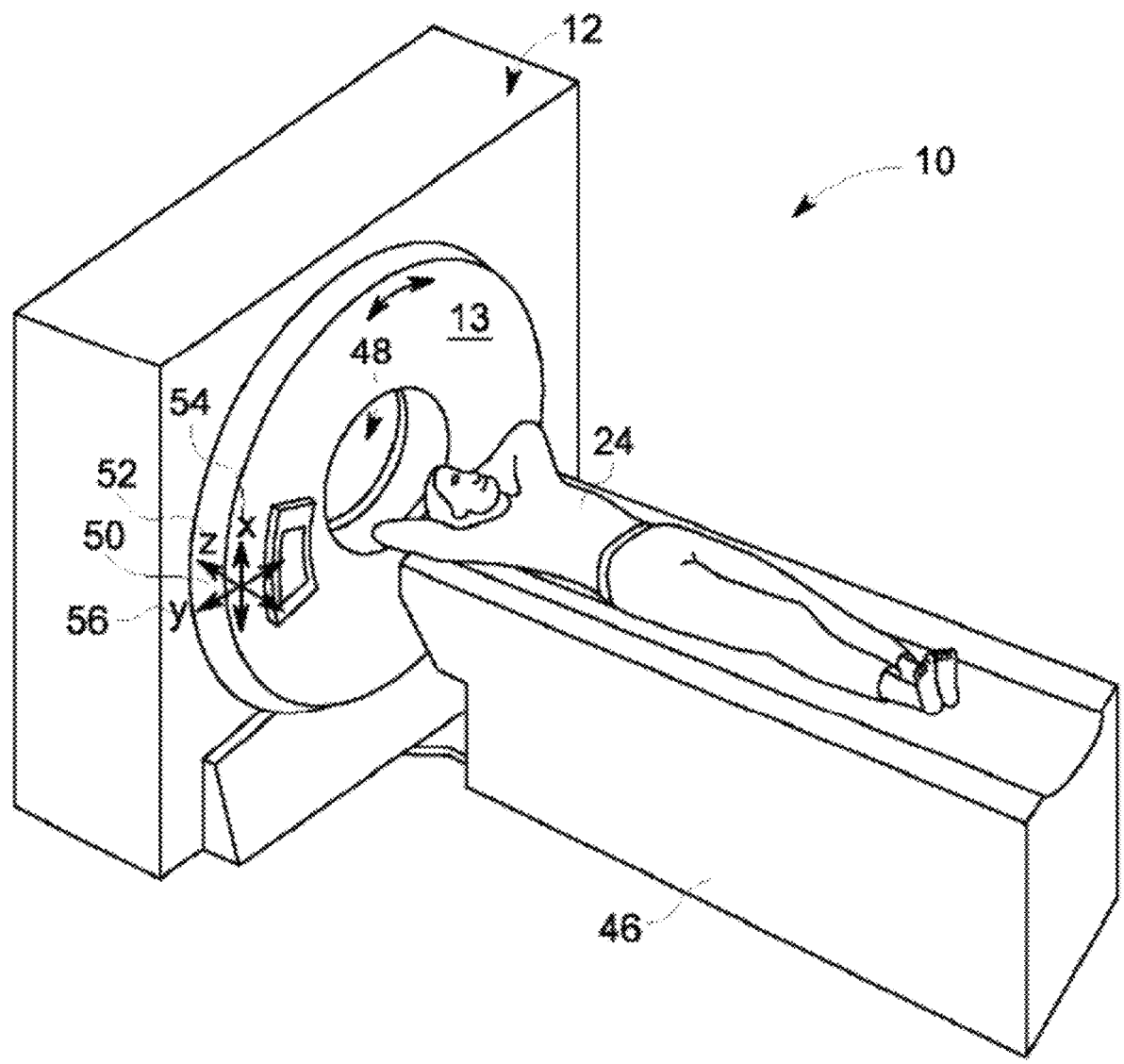
FIGS. 1-2 illustrate an example imaging system to which the methods, apparatus, and articles of manufacture disclosed herein can be applied.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. Overview

Imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

For example, segmentation of radiosensitive organs around a target region is a key step of radiotherapy planning. In clinical practice, segmentation is often performed manually, which may take up to several hours. Automating and improving sensitivity, precision, and accuracy of segmentation would greatly improve efficiency, this task would thus greatly improve efficiency and health and safety for patient care.

During automated segmentation, each voxel is to be analyzed to determine whether the voxel belongs to the segmented organ. Such analysis can be time-consuming. Certain examples increase speed, accuracy, and precision of such analysis by detecting and/or otherwise determining the bounding box of various organs.

Certain examples provide and/or facilitate improved imaging devices which improve diagnostic accuracy and/or coverage. Certain examples facilitate improved image reconstruction and further processing to provide improved diagnostic accuracy.

Machine learning defines a construct that can learn (e.g., make correlations, draw conclusions, etc.) based on a set of data. For example, machine learning can be used to model abstractions within the data set. An example of machine learning is a neural network, which can include visible layers, such as input and output layers of connected nodes, and hidden layers, such as internal layers defined by the network model to connect nodes according to determined correlations, connections, behaviors, etc. Some neural networks are seeded in training with expected correlations, etc. Other neural networks, such as deep learning networks, determine their own correlations from analysis of large data sets. Machine learning techniques, whether deep learning networks or other experiential/observational learning system, can be used to locate an object in an image, understand speech and convert speech into text, and improve the relevance of search engine results, for example.

Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

The term "denoising" or "image denoising" refers to noise reduction and feature preservation in an image. Thus, noise introduced into image data is reduced or eliminated while actual features of a target captured in the image data are preserved to be shown in a resulting image. Image denoising cleans up noise in the image while preserving features for a diagnostic quality image for radiologist and/or other clinician review.

Certain examples use neural networks and/or other machine learning to implement a new workflow for image analysis including body detection in an image (e.g., a two-dimensional and/or three-dimensional computed tomography (CT), x-ray, etc., image), generation of a bounding box around a region of interest, and voxel analysis in the bounding box region. Certain examples facilitate a cloud-shaped stochastic feature-set of a fully-connected network (FCN) in conjunction with multi-layer input features of a CNN using innovative network architectures with gradient boosting machine (GBM) stacking over the FCN and CNN with associated feature sets to segment an image and identify organ(s) in the image.

Deep Learning and Other Machine Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. Description of Examples

Example Imaging Systems

Figure 2:
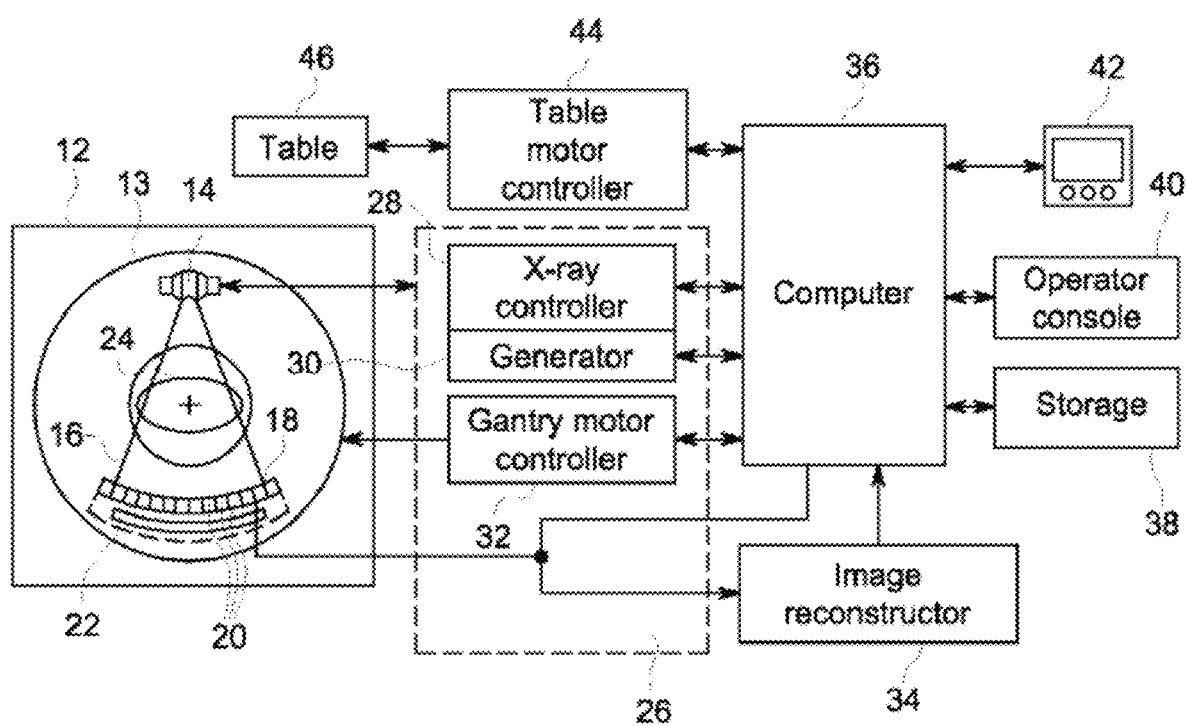

The methods, apparatus, and articles of manufacture described herein can be applied to a variety of healthcare and non-healthcare systems. In one particular example, the methods, apparatus, and articles of manufacture described herein can be applied to the components, configuration, and operation of a computed tomography (CT) imaging system. FIGS. 1-2 illustrate an example implementation of a CT imaging scanner to which the methods, apparatus, and articles of manufacture disclosed herein can be applied. FIGS. 1 and 2 show a CT imaging system 10 including a gantry 12. Gantry 12 has a rotary member 13 with an x-ray source 14 that projects a beam of x-rays 16 toward a detector assembly 18 on the opposite side of the rotary member 13. A main bearing may be utilized to attach the rotary member 13 to the stationary structure of the gantry 12. X-ray source 14 includes either a stationary target or a rotating target. Detector assembly 18 is formed by a plurality of detectors 20 and data acquisition systems (DAS) 22, and can include a collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging x-ray beam and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, table 46 moves a subject 24 through a gantry opening 48, or bore, in whole or in part. A coordinate system 50 defines a patient or Z-axis 52 along which subject 24 is moved in and out of opening 48, a gantry circumferential or X-axis 54 along which detector assembly 18 passes, and a Y-axis 56 that passes along a direction from a focal spot of x-ray tube 14 to detector assembly 18.

Thus, certain examples can apply machine learning techniques to configuration and/or operation of the CT scanner 10 and its gantry 12, rotary member 13, x-ray source 14, detector assembly 18, control mechanism 26, image reconstructor 34, computer 36, operator console 40, display 42, table controller 44, table 46, and/or gantry opening 48, etc. Component configuration, operation, etc., can be monitored based on input, desired output, actual output, etc., to learn and suggest change(s) to configuration, operation, and/or image capture and/or processing of the scanner 10 and/or its components, for example.

Example Learning Network Systems

Figure 3:
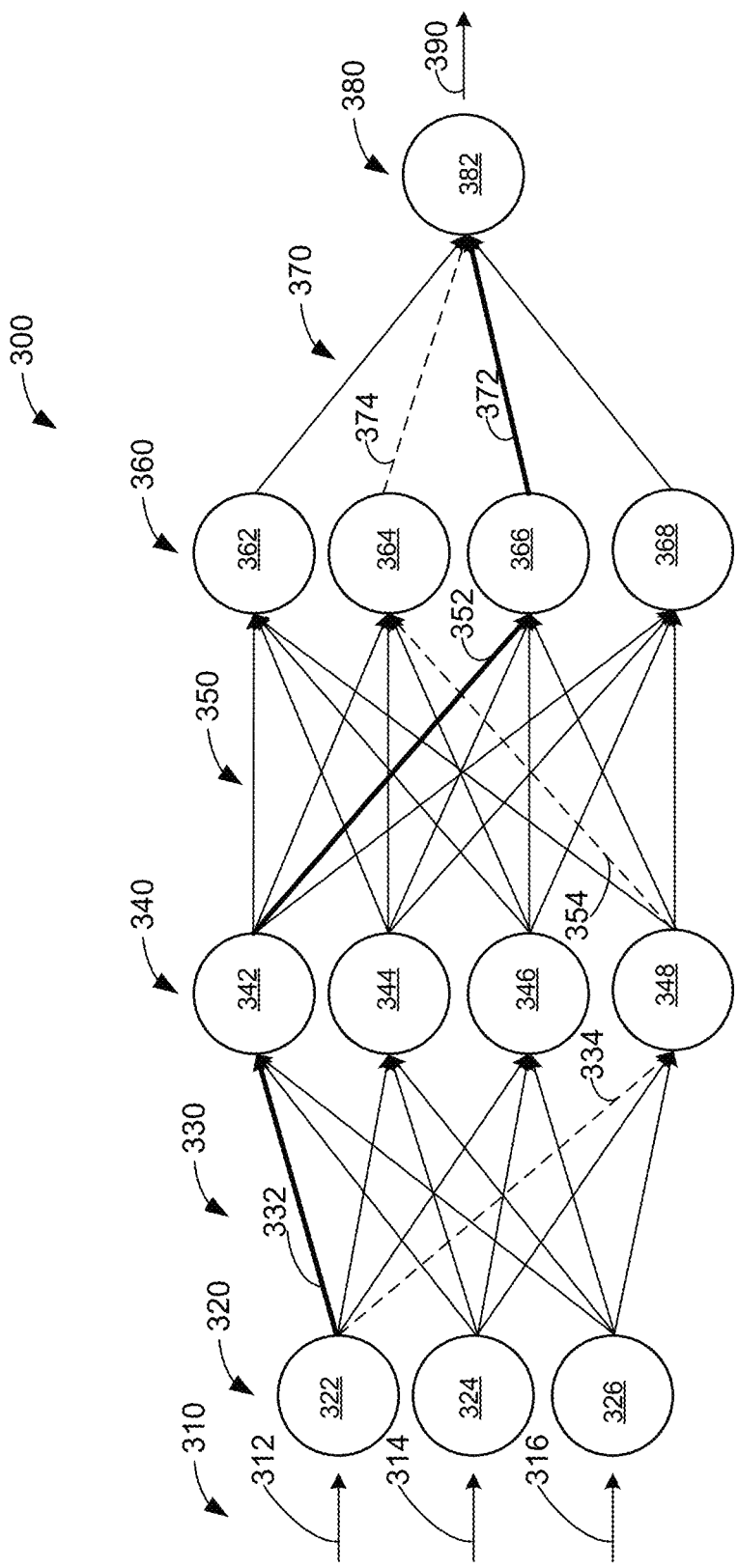
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
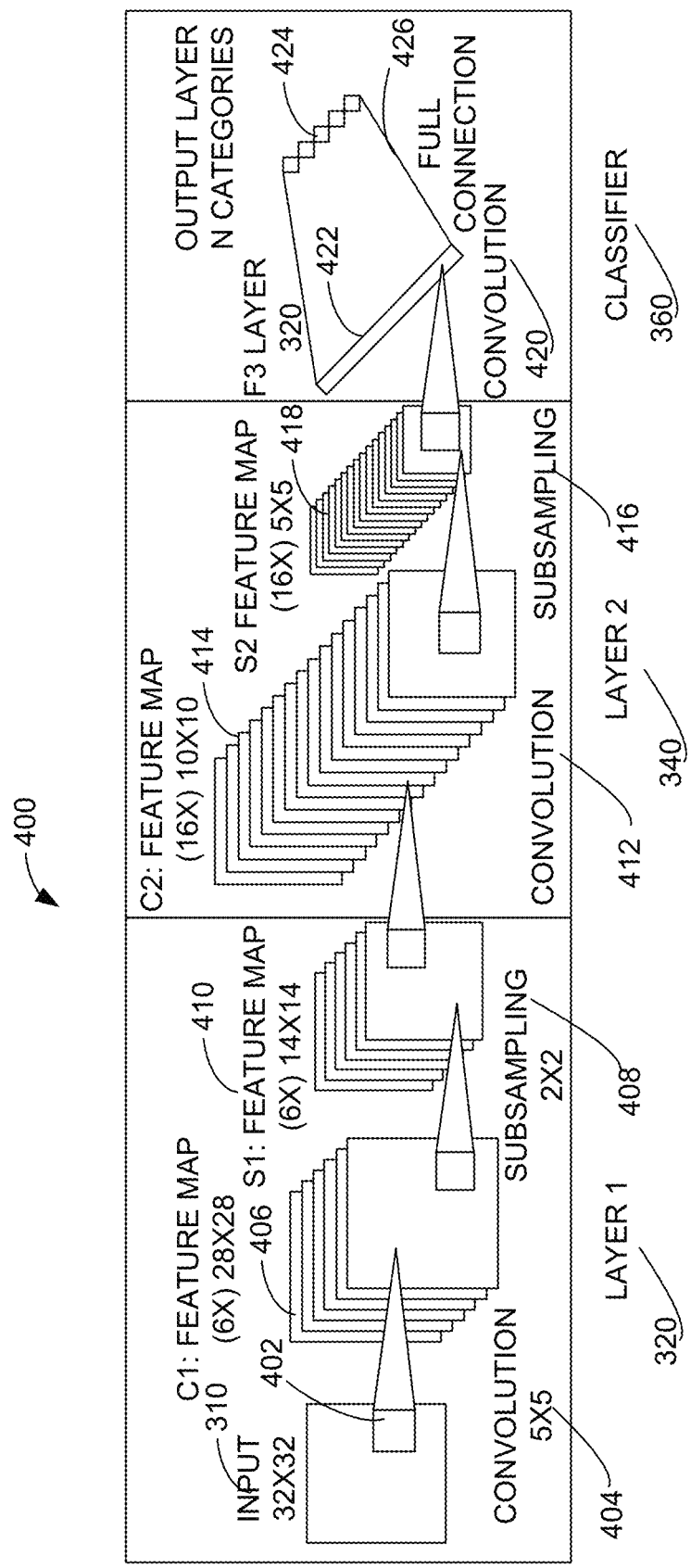
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer 380. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
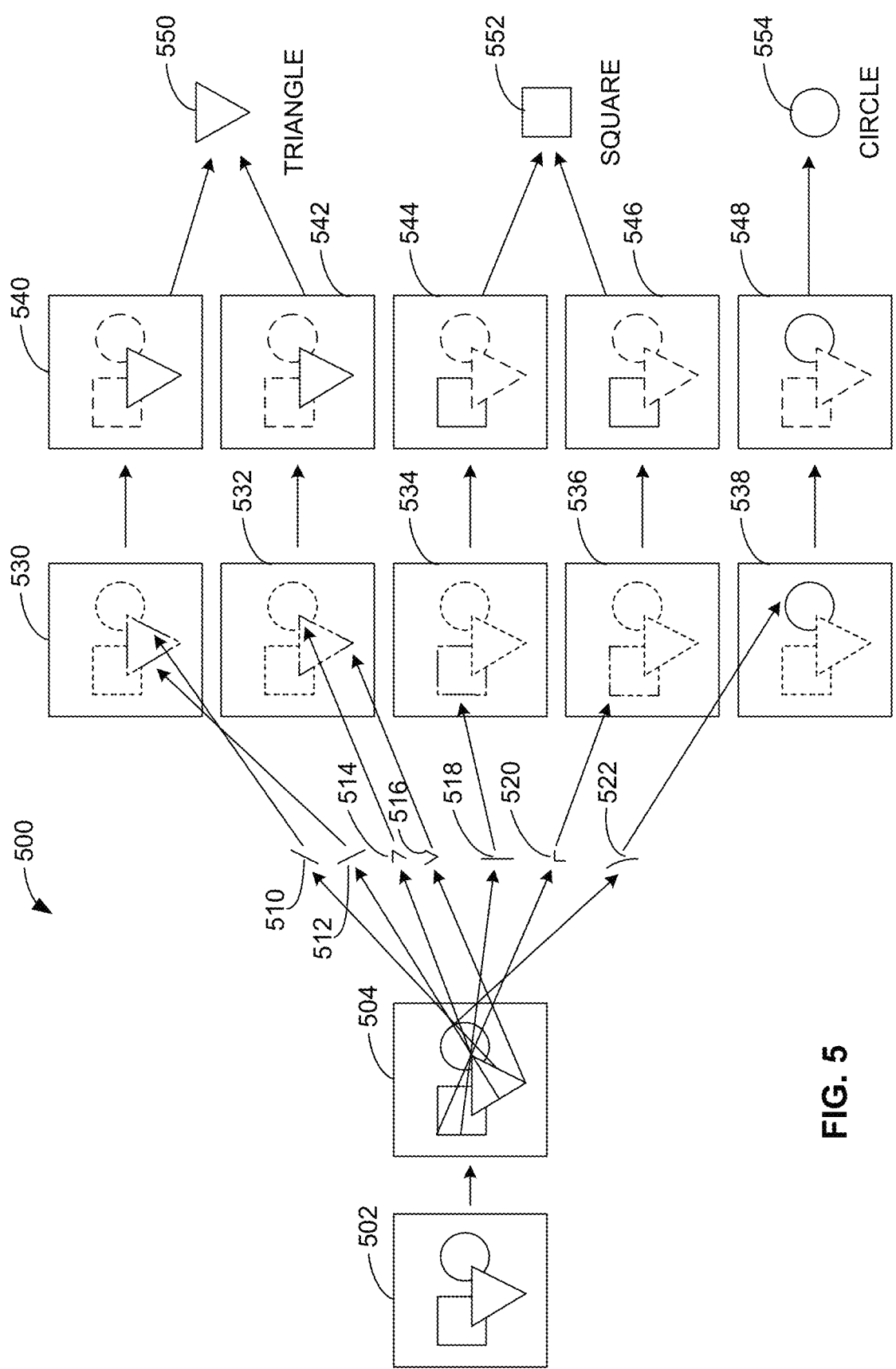
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

Figure 6A:
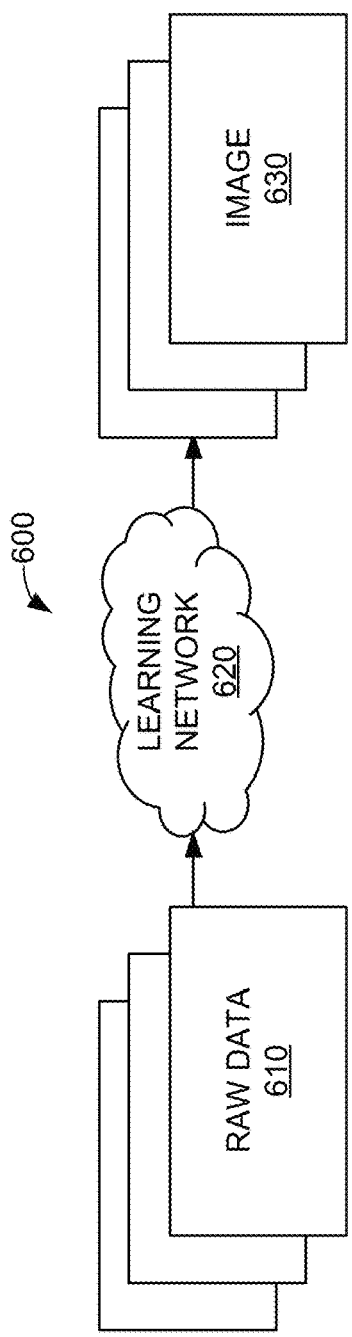
FIG. 6A illustrates an example configuration to apply a learning network to process and/or otherwise evaluate an image.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw image data 620 into a resulting image 630 (e.g., a "good quality" image and/or other image providing sufficient quality for diagnosis, etc.). The learning network 620 includes nodes and connections (e.g., pathways) to associate raw data 610 with a finished image 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc.

Figure 6B:
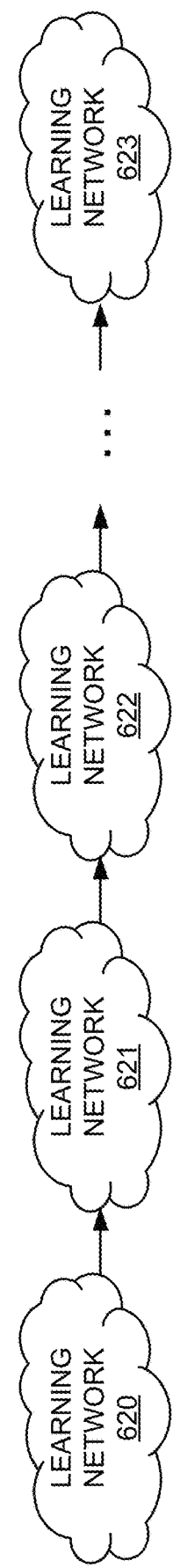
FIG. 6B illustrates a combination of a plurality of learning networks.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
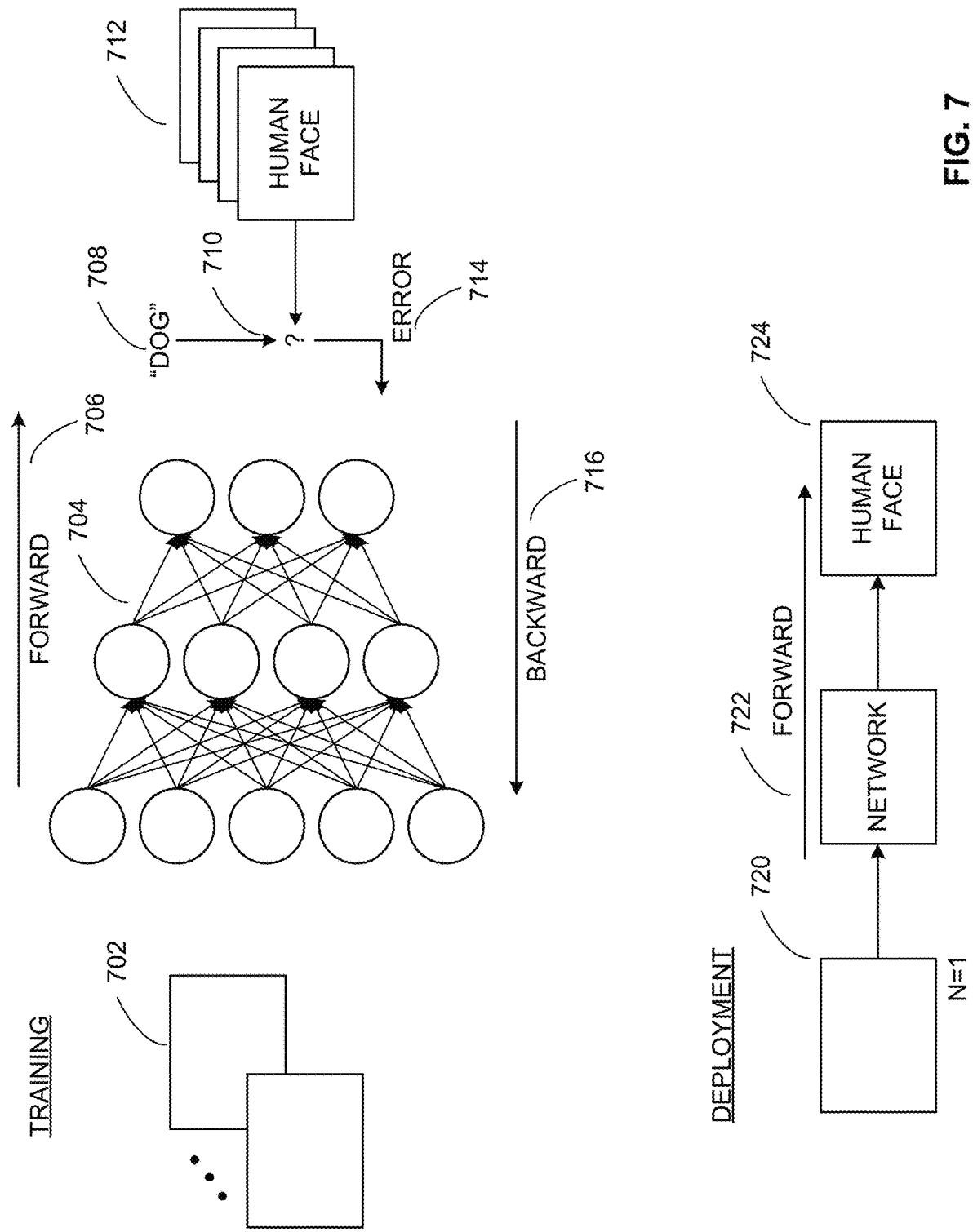
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a dog 708. In training, the network result 708 is compared 710 to a known outcome 712. In this example, the known outcome 712 is a human face (e.g., the input data set 702 represents a human face, not a dog face). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a human face 724.

Figure 8:
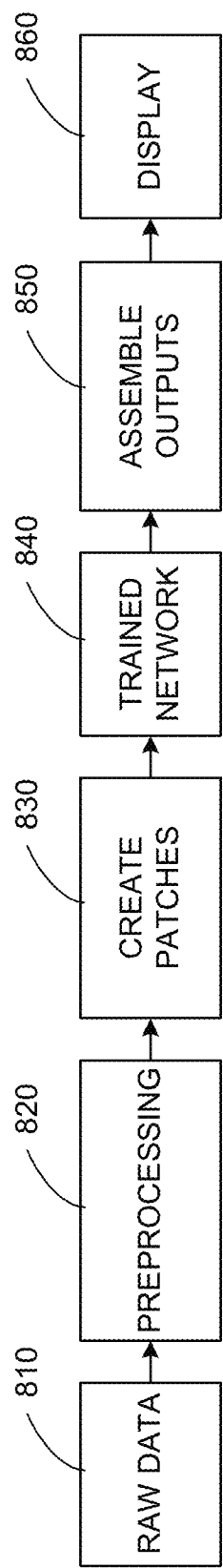
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
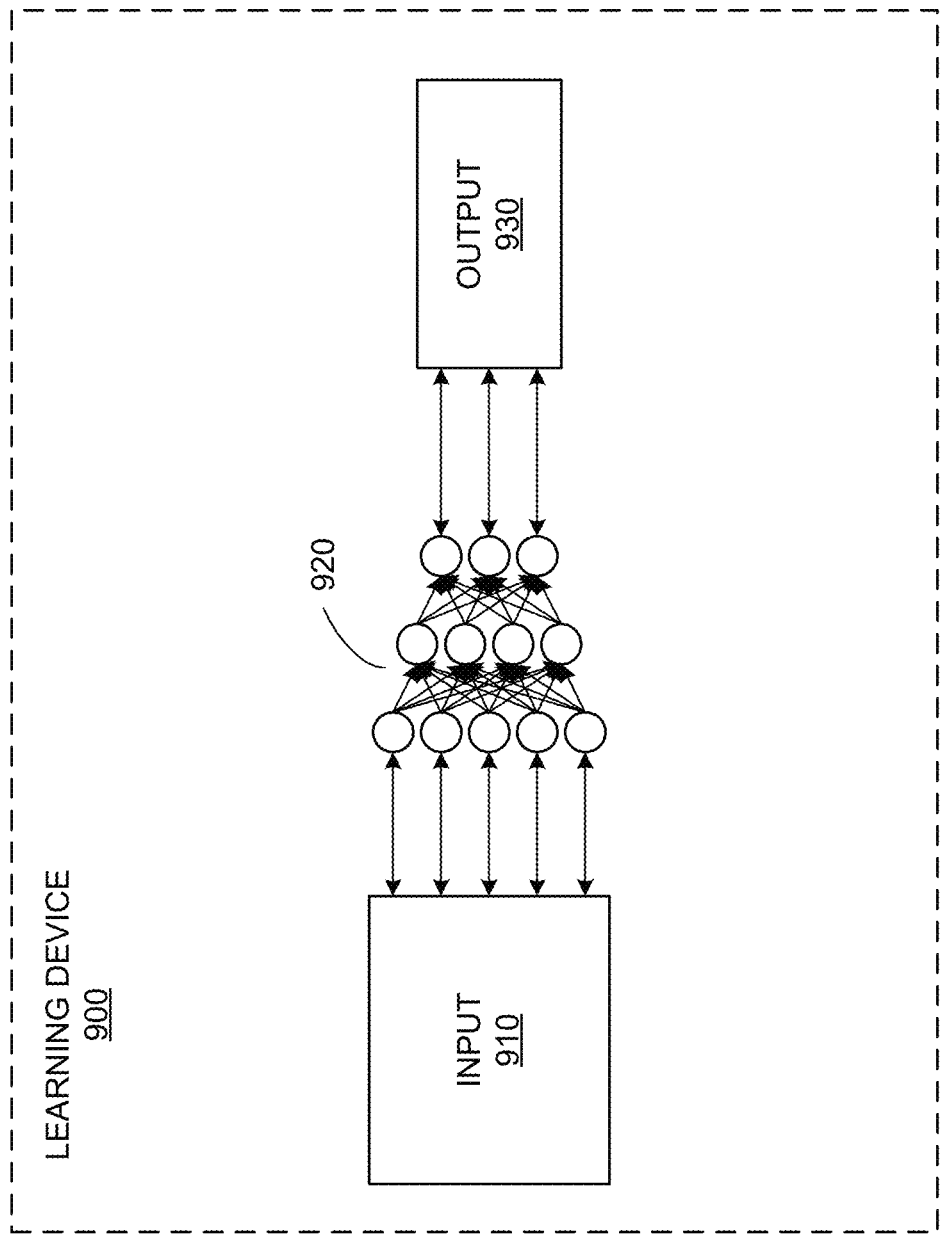
FIGS. 9A-9C illustrate various deep learning device configurations.
Figure 9B:
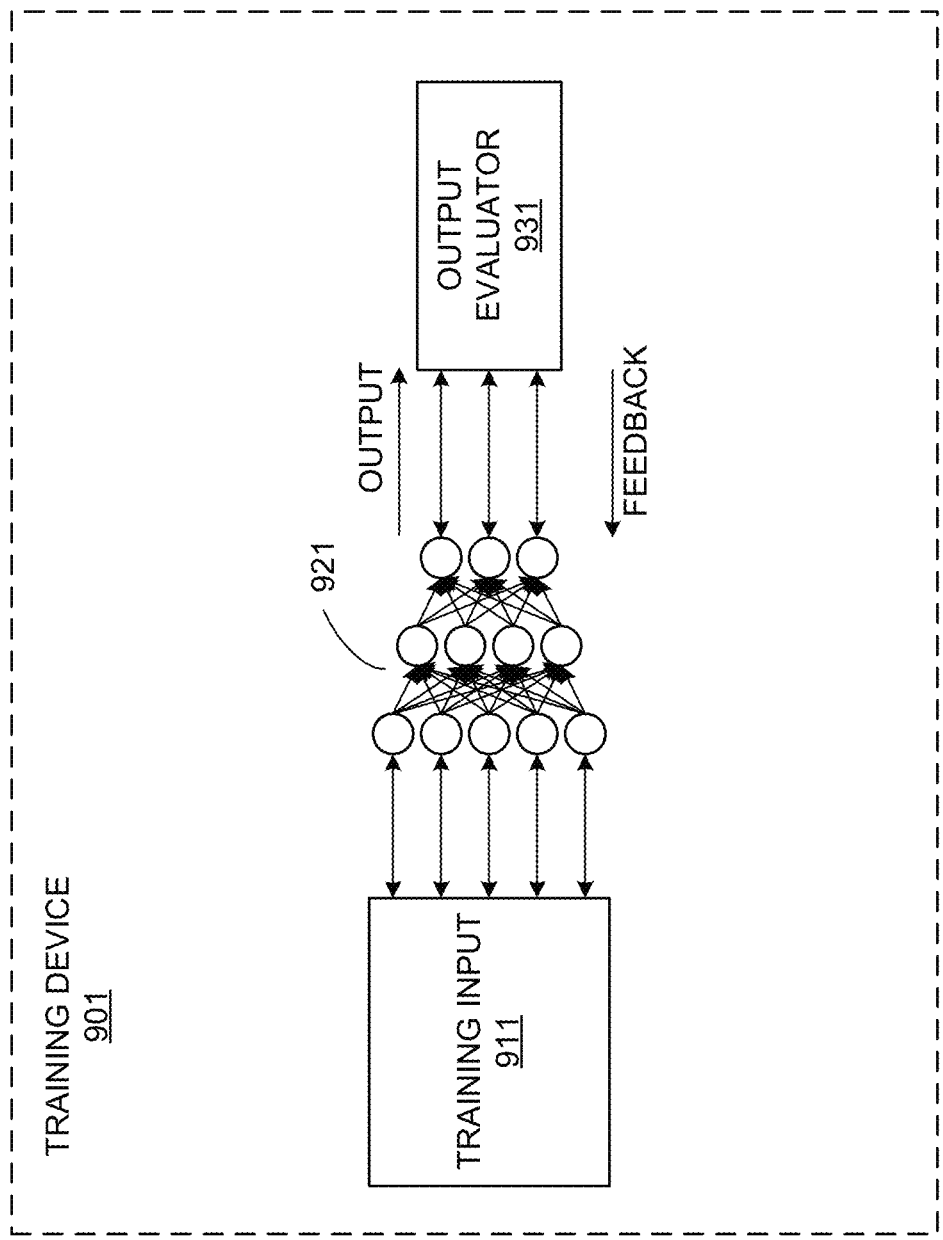
Figure 9C:
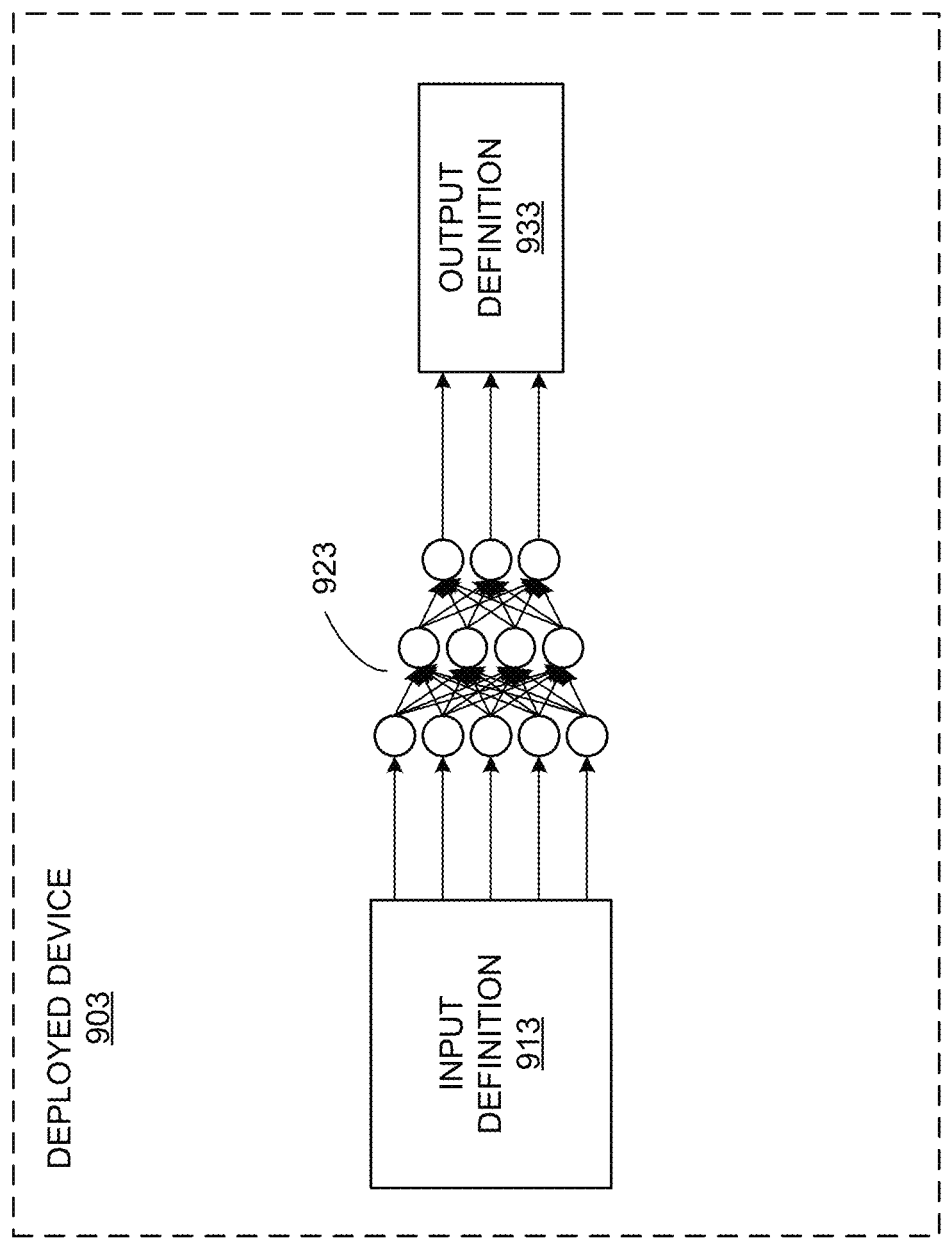

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definitions 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Image Denoising Systems and Methods

Image denoising processes obtained image data to reduce noise in the image data while preserving features of the patient and/or other target captured by the imaging system in the image data. Image denoising can be facilitated using wavelet transform, statistical methods, deep learning, etc. For example, wavelet transformation uses thresholds (e.g., sub-band coefficient thresholds) to remove noise uniformly spread throughout image data coefficients while leaving image data concentrated in a few large coefficients. As an alternative, wavelet transforms can use a Bayesian framework of non-linear estimators to provide noise reduction and feature preservation by employing an accurate statistical description of image data signal and noise components. Statistical methods for image denoising model image pixel values according to a distribution, such as a Gaussian distribution in which a grayscale value for a pixel in an image is normally distributed with a mean equal to an average grayscale value of its neighborhood pixels with a given variance. Deep learning can be applied to process image data for noise reduction, improved resolution, etc., via a CNN and/or other learning model.

Image denoising is particularly of interest in CT imaging as removing noise from an image translates to radiation dose saving in the image acquisition process. Conventional image denoising methods focus on hand-designed image filters (mostly non-linear such as GE's ASiR-V™). However, conventional image denoising methods have many disadvantages including producing a patchy texture and jagged edges in resulting denoised images. Certain examples disclosed and described herein overcome these disadvantages to provide diagnostic quality, denoised images.

Deep learning technique have been utilized in many applications, including image denoising. Some deep learning denoising methods show unique benefits over conventional denoising methods, such as delightful texture and smooth edges in denoised images. Most deep learning methods rely on large training data set to be successful. However, besides the difficulties in obtaining large amount of training data and long training time in handling the large amount of training data, using a population of patient data to train a denoising model has another high risk: the neural network may learn anatomical structures from the training data and try to generate similar structures when performing the denoising task by inferencing. Certain examples provide systems and methods that generate training data and perform denoising task(s) from the same patient CT scan without generating anatomical structures that do not belong to the patient and were not found in the original image data, for example.

If a different patient is used, for example, the network model risks copying anatomical features from the other patient into the current patient scan. If a lesion is copied from training data into a healthy patient, a mis-diagnosis will occur, for example. Certain examples use the same patient's data for training and inference, which avoids accidental or inadvertent importing of other patient image features through the deep learning training process.

Thus, in certain examples, rather than leveraging a large data set spanning several patients, which is typically how deep learning is conducted, a single patient is used for patient-specific training of a CNN or other neural network for application of the deployed network model to images obtained from that particular patient. With patient-specific network training, much less data can be used to effectively train the network, and network weights and connections are developed for that particular patient, improving its applicability to that patient. One patient's data can be used to train a model for him/herself and provide sufficient detail to enable denoising of that patient's images.

Noisy patient images can be generated in many ways to include known noise. For example, noise can be added into patient images in a projection domain and/or an image domain. Noise can be generated in the projection domain and/or the image domain noise by simulation (e.g., via analytical calculation and/or Monte Carlo simulation based on noise modellings, etc.) and/or real acquisition (e.g., by repeating scans from phantoms/animals/cadavers, using a single scan from a phantom with uniform regions, etc.), for example. Different phantoms/animals/cadavers/etc. can provide different patterns of noise. Phantoms can be simple phantoms (e.g., water/polyester in a cylinder/oval or with one or more inserts, etc.) or anthropomorphic phantoms (e.g., a Lungman phantom, a Kyoto whole body phantom, etc.).

An output of the training network is an identification of the noise that was added to the low-noise patient image. The identified noise is matched to the actual noise added to determine accuracy of the model. In certain examples, an output of the network model is only noise, and that noise corresponds to an estimate of noise present in the image volume. The output can be compared to a known clean or reference image (e.g., from a phantom or verified from the patient, etc.) to help ensure that no artifact is left in the image when the identified noise is removed, for example. The resulting image can also be compared to a verified, reference image to help ensure that actual image data is not being removed along with the noise, for example.

By training the network, the deployed network model can identify noise in input image data. A network model with accurate identification of the noise can be deployed to be applied to images of the same patient used to train the network model and/or a different patient, for example. The model can be applied to thin and/or thick slice patient image(s) to estimate noise in those patient image(s) (e.g., even if the network model is trained on thick slices, it can be applied to detect and remove noise in thin image slices).

In certain examples, a convolutional neural network (CNN) can be used for noise identification and denoising of a patient image. For example, a 17-layer CNN including 64 outputs for each two-dimensional (2D) convolutional layer and a 3×3 kernel size for each layer except the last convolutional output layer with a single output) can be used. In this example, rectified linear unit (ReLU) activation is used in the first 16 layers of the example CNN, and batch normalization is used in the last layer of the CNN. Noisy training data is generated by adding noise to the FBP reconstructions and then break into 40×40 small patch images. By comparing the noisy images with the images before adding noise, one can have the ground truth of the noise pattern added into the training data.

For training, the noisy images are used as input to the neural network and the ground truth of noise is used as training target output/result. A mean squared error (MSE) loss function and stochastic gradient descent Adam optimizer can be used, for example, and the training can stop after pre-set epochs are reached. Thus, the CNN can be used in iterative training to pass through the training data set followed by testing with a verification set to form a single epoch. Multiple epochs can be executed to train the network model for denoising deployment.

In this example, an inferencing input size for denoising using the CNN can be different than the training input size. For example, 512×512 filtered back projection (FBP) images (e.g., after back-projection has been performed on the image data to run source projections back through the image to reconstruct the source and filtered to eliminate blurring or star-like artifacts, etc.) can be used as input to the CNN, and estimated noise images can be generated by inferencing. Then, the estimated noise images are subtracted from the input images to produce denoised images. Finally, denoised images are post-processed to generate final output images.

Thus, in this example, a patient scan is obtained, and no other patient scans or additional patient data are needed to process the image and train the network model. A water phantom scan can be obtained once for the particular scanner and stored as calibration data on the scanner for use with each patient's image scan until the scanner configuration is changed. Thus, rather than a large data set, typically required for deep learning, a single patient scan (or multiple scans for that single patient) can be used to train a deep learning network for denoising of patient images.

Figure 10:
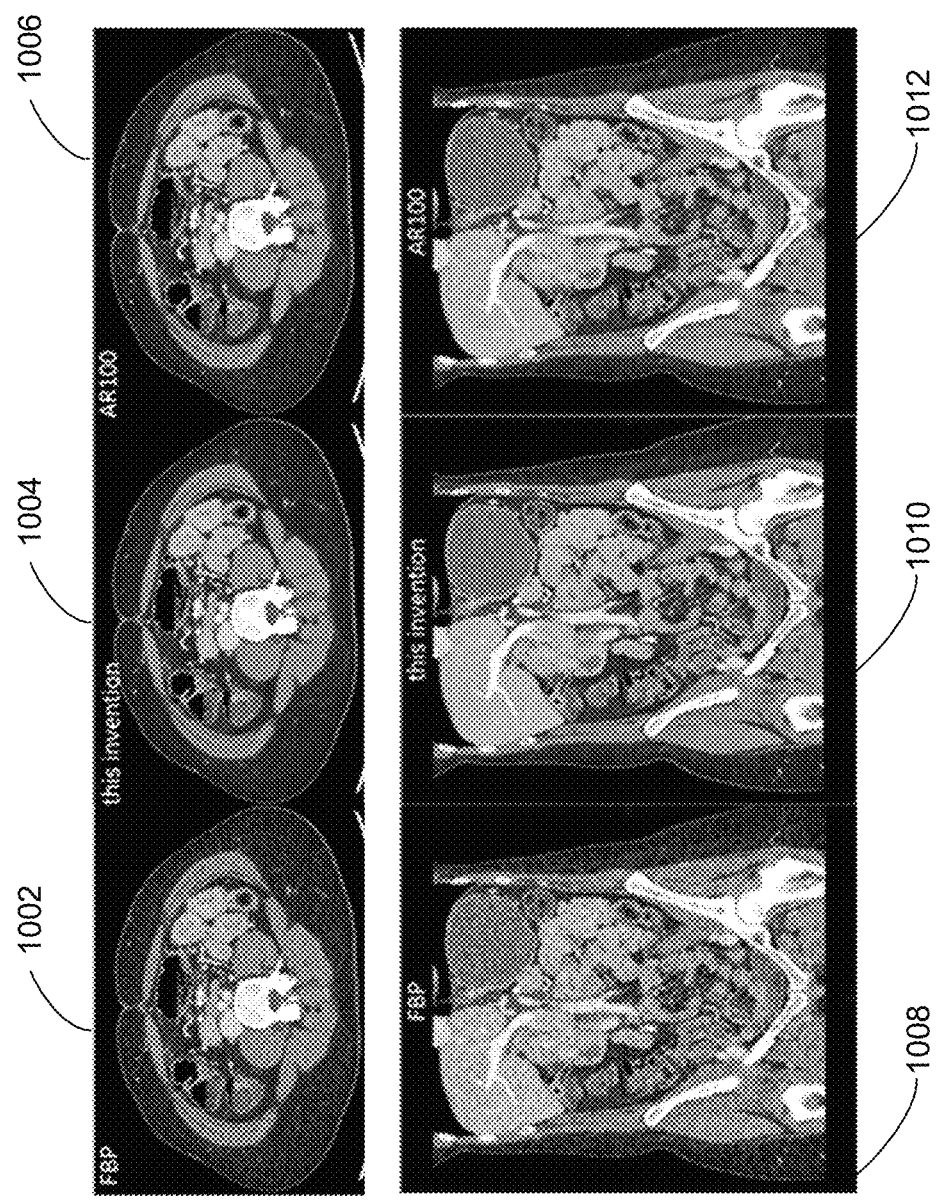
FIG. 10 shows results of a comparison between deep learning network-driven image denoising and other reconstruction techniques.

FIG. 10 shows results of a comparison between a) FBP reconstruction, b) deep learning network-driven denoising, and c) ASiR-V 100% reconstruction. As shown in the example of FIG. 1, abdominal scans processed with FBP reconstruction 1002, deep learning network denoising 1004, and ASiR-V reconstruction 1006, as well as anteroposterior (AP) views of the abdomen/pelvis processed with FBP reconstruction 1008, deep learning network denoising 1010, and ASiR-V reconstruction 1012 can be compared to illustrate the improved accuracy of the deep learning network-driven denoising technique.

Figure 11:
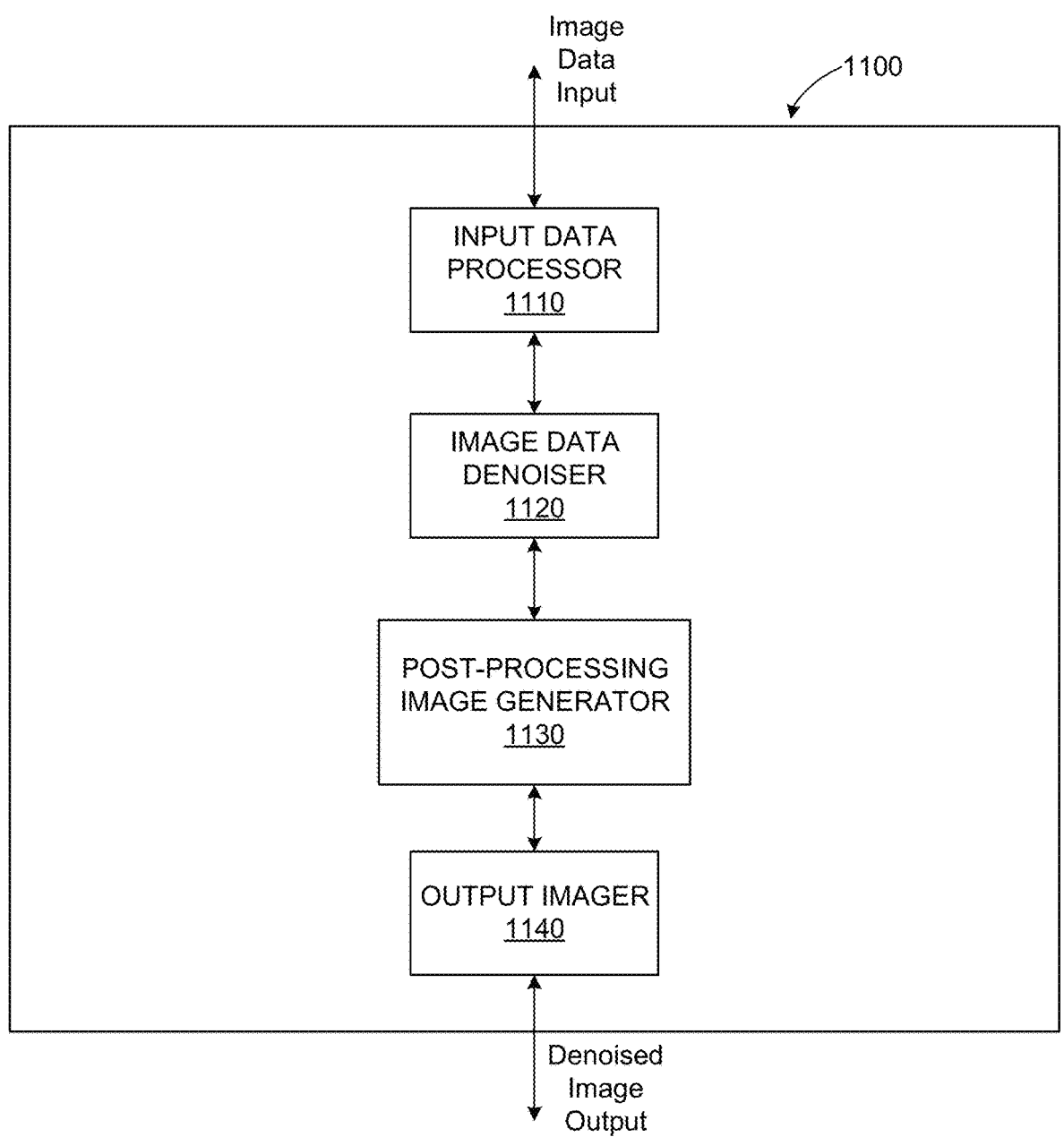
FIG. 11 illustrates an example image processor apparatus to process and denoise image data obtained from an imaging modality

FIG. 11 illustrates an example image processor apparatus 1100 to process image data obtained from an imaging modality (e.g., CT, MR, ultrasound, x-ray, etc.) and remove noise/artifacts from the image. The example apparatus 1100 includes an input data processor 1110, an image denoiser 1120, a post-processing image generator 1130, and an output imager 1140. The example input data processor 1110 is to process incoming image, noise, and other data from an imaging modality, image archive, electronic medical record, etc. Incoming data can be parsed, formatted, organized, refined, etc., for further processing by the image processor 1100. The example image denoiser 1120 takes the processed input data, including a patient image and noise information for the corresponding imaging modality and processes the image based on the noise information to identify noise/artifacts in the patient image. The example post-processing image generator 1130 takes the information regarding noise in the patient and post-processes the image to remove noise from the image and apply post-processing (e.g., contrast, brightness, region of interest identification, etc.) to produce an image to be output by the example output imager 1140. For example, the output imager 1140 can provide the output image to an image reading workstation, another image viewer, an image processing system, a clinical decision support system, an image archive, electronic medical record, etc.

Figure 12:
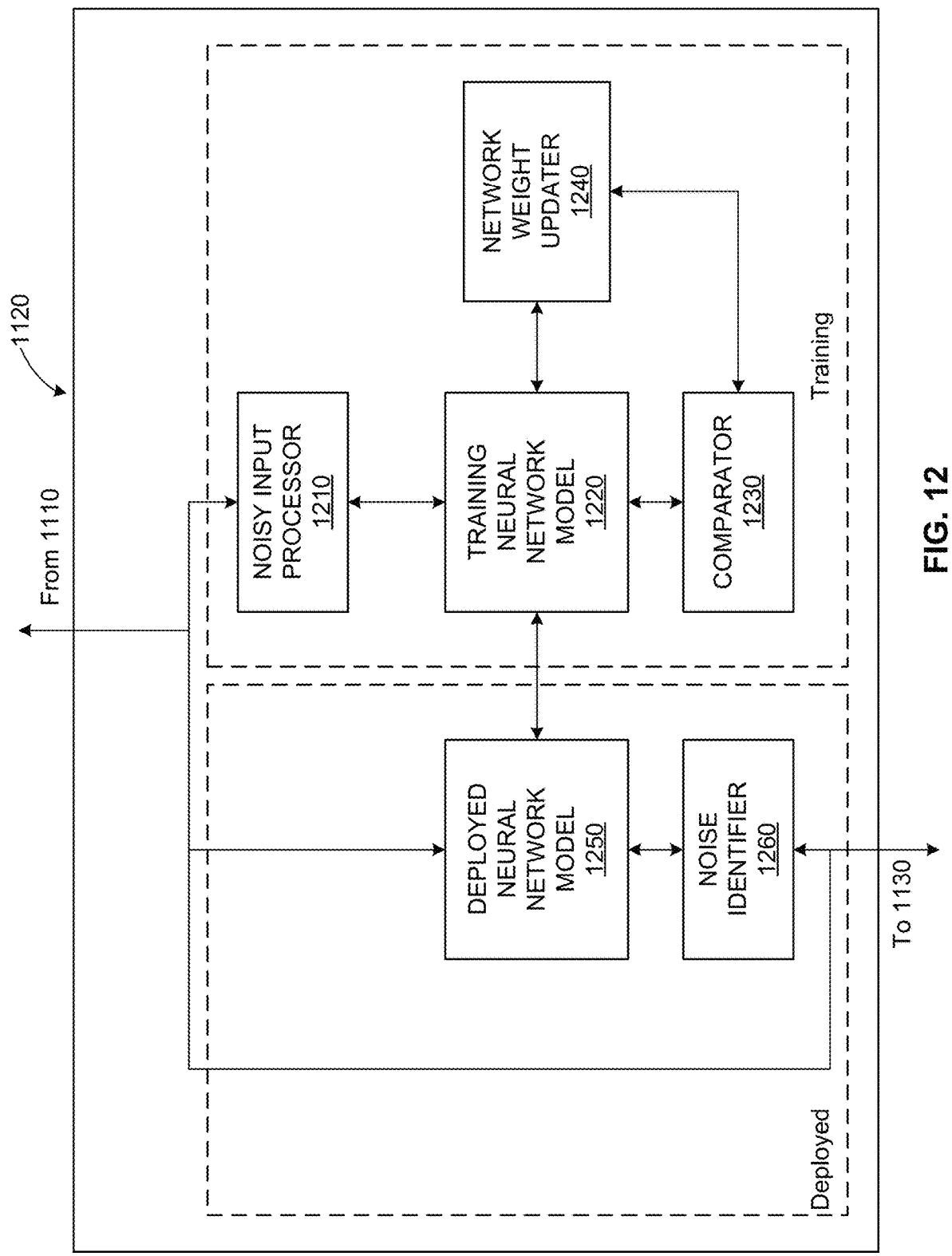
FIG. 12 depicts an example implementation of the image denoiser of the example of FIG. 11.

FIG. 12 depicts an example implementation of the image denoiser 1120 of the example of FIG. 11. As shown in the example of FIG. 12, the image denoiser 1120 includes a noisy input processor 1210, a training neural network model 1220, a comparator 1230, a network weight updater 1240, a deployed neural network model 1250, and a noise identifier 1260. In operation, image, noise, and other data from the input data processor 1110 are provided to the noisy input processor 1210, which combines the noise information with patient image data to form a noisy image as input to train the training neural network model 1220. The training neural network model 1220 processes the noisy image data through convolution, filtering, etc., to identify the noise in the noisy image data. The training neural network model 1220 extracts and outputs the noise, which is fed to the comparator 1230. The comparator 1230 compares the noise extracted by the training neural network 1220 with an expected, known, or "ground truth" noise value to determine an accuracy of the network model 1220. Feedback from the comparator 1230 indicating how close or how far the neural network model 1220 is from correctly identifying the known noise in the noisy image can be provided to the network weight updater 1240, which can adjust network weights of the training model 1220 to adjust operation of the model 1220 with respect to the noisy image data. When the comparator 1230 is satisfied that the training model 1220 is accurately identifying and quantifying the noise in the noisy image, the training neural network model 1220 can be instantiated as a data structure and deployed as the deployed neural network model 1250. The deployed neural network model 1250 can then process including image data to identify noise in the patient image from the image modality. The noise identifier 1260 can quantify the noise information and, packaged with the image, send the information to the post-processing image generator 1130 to generate the patient image with noise/artifacts removed.

While example implementations are illustrated in conjunction with FIGS. 1-12, elements, processes and/or devices illustrated in conjunction with FIGS. 1-12 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components disclosed and described herein are shown in conjunction with at least FIGS. 13-16. In the examples, the machine readable instructions include a program for execution by a processor such as the processor 1712 shown in the example processor platform 1700 discussed below in connection with FIG. 17. The program may be embodied in machine readable instructions stored on a tangible computer readable storage medium such as a CD-ROM, a floppy disk, a hard drive, a digital versatile disk (DVD), a Blu-ray disk, or a memory associated with the processor 1712, but the entire program and/or parts thereof could alternatively be executed by a device other than the processor 1712 and/or embodied in firmware or dedicated hardware. Further, although the example program is described with reference to the flowcharts illustrated in conjunction with at least FIGS. 13-16, many other methods of implementing the components disclosed and described herein may alternatively be used. For example, the order of execution of the blocks may be changed, and/or some of the blocks described may be changed, eliminated, or combined. Although the flowcharts of at least FIGS. 13-16 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) of at least FIGS. 13-16 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of at least FIGS. 13-16 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 13:
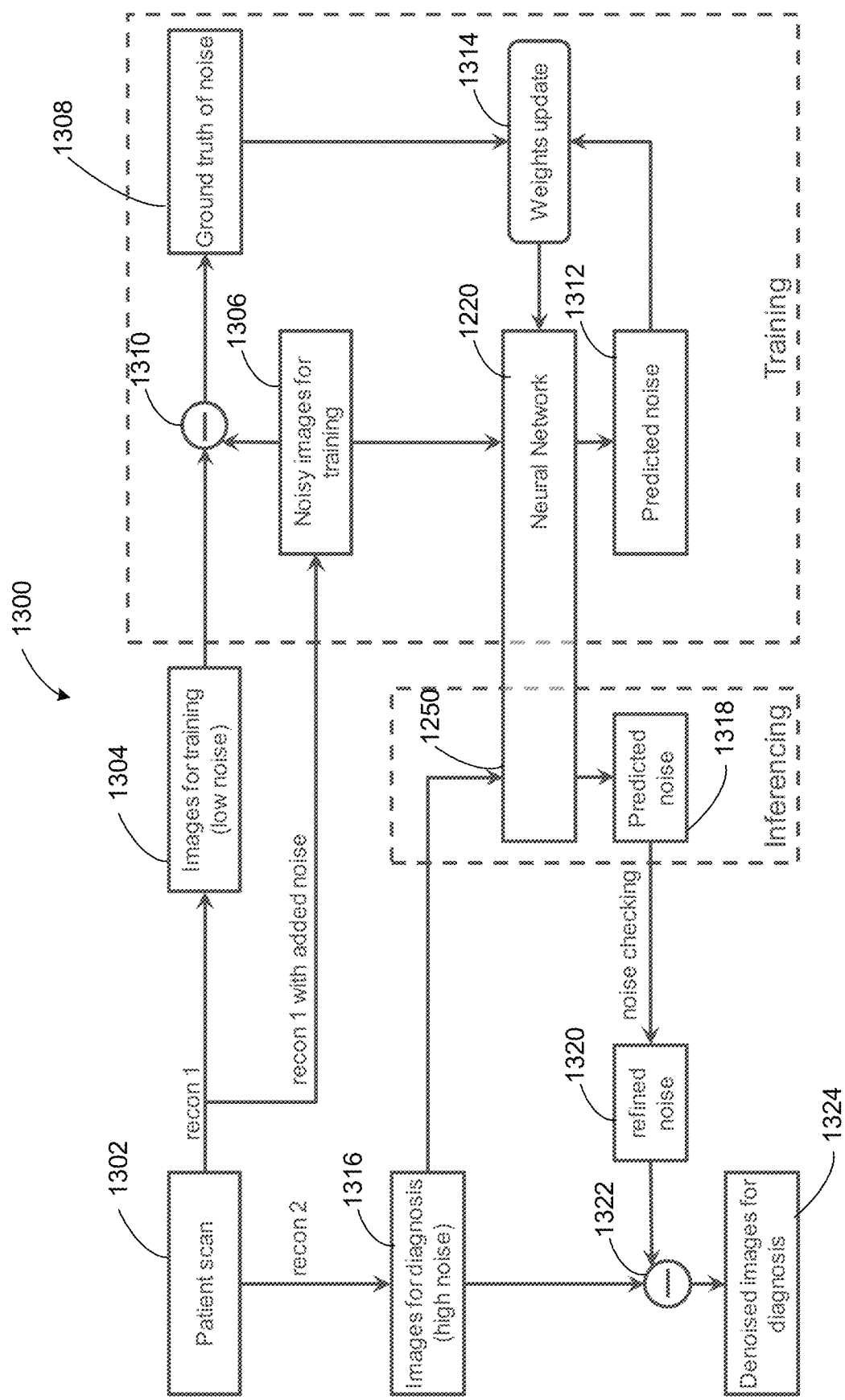
FIGS. 13-16 illustrate flow diagrams of example methods to process a patient image using a neural network to identify and eliminate noise from that patient's images.

FIG. 13 illustrates a flow diagram of an example method 1300 to process a patient image using a neural network 1220, 1250 (e.g., a CNN and/or other deep learning network) to identify and eliminate noise from that patient's images. At block 1302, a first image volume of a patient is obtained (e.g., from a CT scanner, MR scanner, X-ray machine, ultrasound probe, etc.). This image volume has high noise. A first set of reconstruction parameters can be used to obtain and produce the first image volume, for example. At block 1304, a different set of reconstruction parameters is used to produce a second image volume with low noise.

At block 1306, the reconstruction parameters used at block 1304 to generate the second image volume can be reused in combination with noise added during the image reconstruction. Thus, the second image volume in combination with noise produces a noisy image. The noisy image reconstructed at block 1306 can be used as input to train the CNN 1220, for example. At block 1308, quantified or "known" noise can be determined by subtracting 1310 the second image volume from the noisy image to reconstruct the added noise.

At block 1312, predicted noise is output by the CNN 1220, representing the network's attempt to identify the noise in the noisy image input 1306 based on analysis of the noisy image data in the convolutional neural network 1220. Based on how closely the CNN 1220 has (or has not) identified the noise 1312 in the noisy input 1306, at block 1314, network weights for nodes, connections, etc., in the CNN 1220 can be adjusted. The CNN 1220 can then operate again on the noisy input 1306 to determine predicted noise 1312, and network weights can be further adjusted 1314 if warranted.

When the CNN 1220 is trained to identify noise 1312 in the image with sufficient accuracy (e.g., a loss function value or a number of trained epochs reaches a preset threshold, etc.), the network can be deployed. The deployed CNN 1250 receives a high noise image volume (block 1316) to be used for diagnosis and processes the patient image to generate predicted noise (block 1318) for the image. At block 1320, the predicted noise 1318 can be checked and/or otherwise quantified to generate refined noise. At block 1322, the refined noise 1320 is subtracted from the patient image 1316 to generate a denoised image volume for diagnosis (block 1324).

Figure 14:
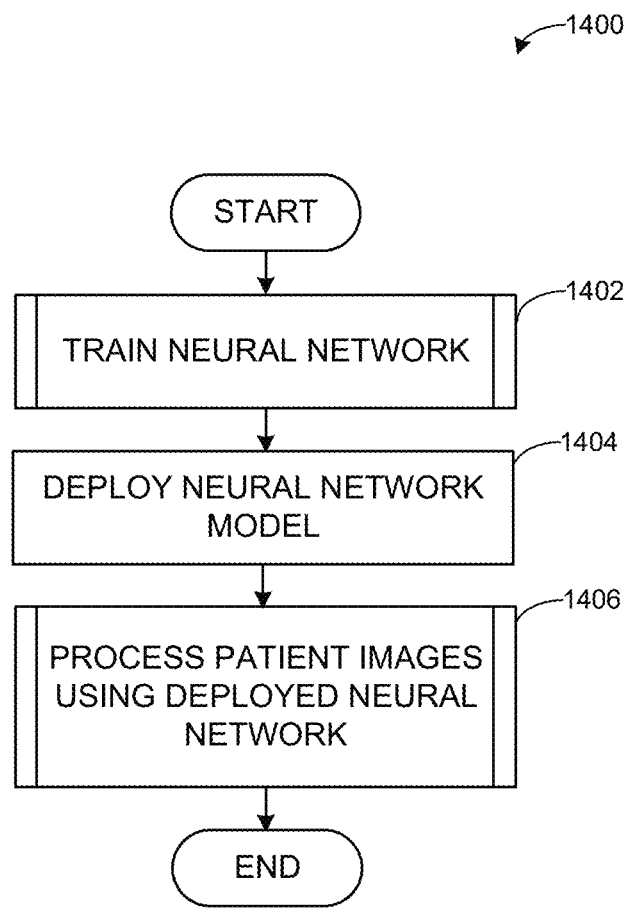

FIG. 14 illustrates a flowchart of an example method 1400 to denoise a patient's images using a deep neural network model trained on that patient's image data for the imaging modality. At block 1402, the deep neural network 1220 is trained on the patient's own image(s). Thus, rather than requiring a large data pool of multiple images from multiple patients, the deep neural network 1220 can be trained using the patient's own image from an imaging scanner, and noise information known for that imaging scanner. Once the network 1220 has been trained and verified to properly identify the noise introduced in the patient image by the scanner (e.g., within a tolerance or margin of error such that noticeable noise is left undetected in the image by the network 1220 and no noticeable image data is mistakenly characterized as noise, etc.), the training network 1220 can be deployed (block 1404) as a deep neural network model 1250 to be used to process incoming patient images (block 1406).

Figure 15:
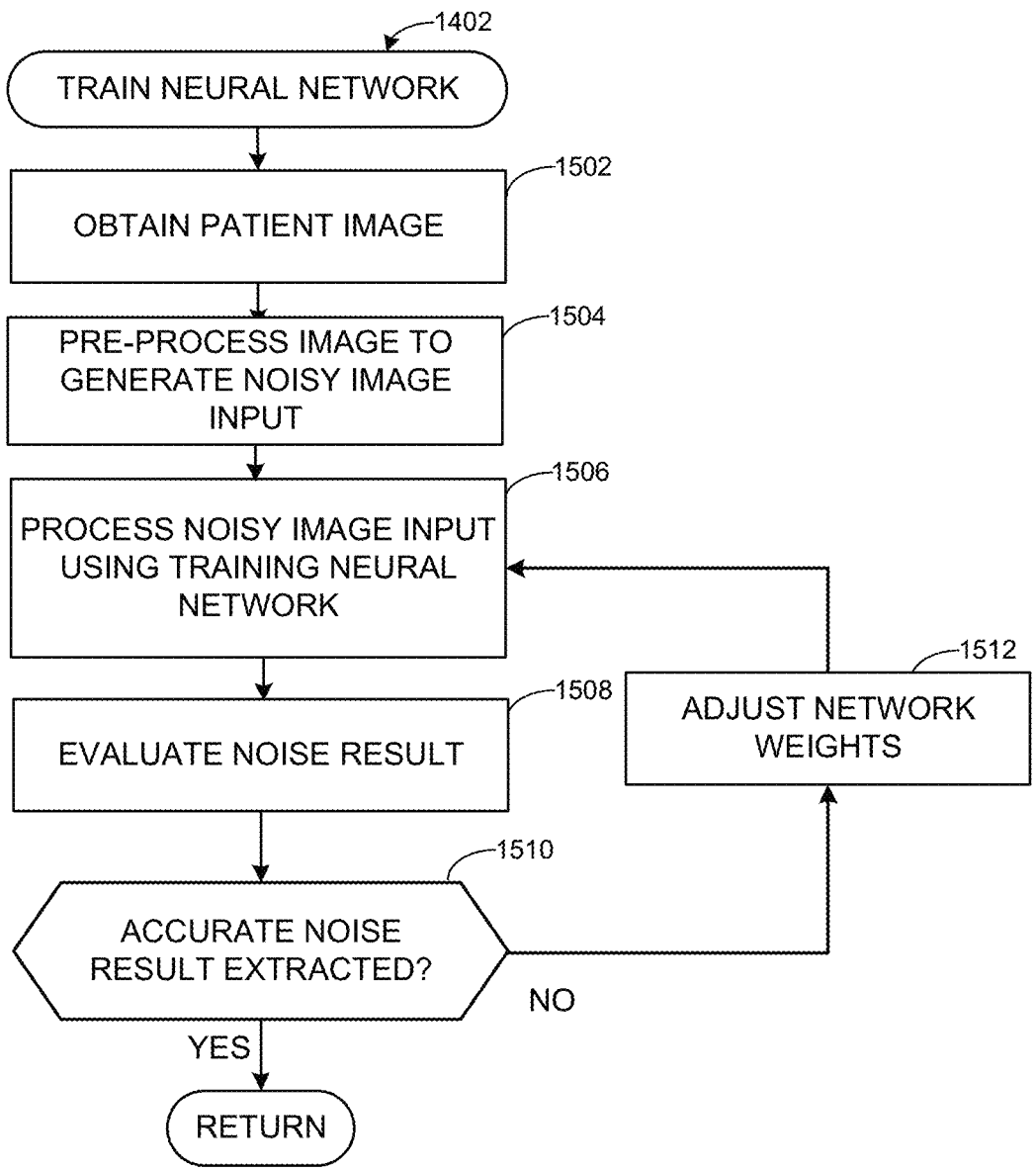

FIG. 15 illustrates an example implementation of training the deep neural network (block 1402) described above with respect to FIG. 14. In this example, at block 1502, a patient image is obtained (e.g., an image volume for the patient obtained as a thin slice, thick slice, etc.). At block 1504, the patient image is pre-processed to prepare the image for the training deep neural network 1220. For example, the thin image slice can be thickened (e.g., by combining thin slices, extrapolating additional data, etc.) to reduce noise in the patient image. One or more patches can be extracted from the patient image, for example. Noise (e.g., simulated and/or measured from a phantom using the scanner, etc.) is added to the patient image to form a noisy image input for processing by the training network 1220.

At block 1506, the noisy image input processed using the training neural network 1220. For example, convolutions, filters, etc., are applied via kernels to the noisy image input to identify and quantify the noise in the image. An output of the network 1220 is the identification/quantification of the noise.

At block 1508, the noise result output by the training network is evaluated against known information regarding the noise that was introduced in the pre-processing. For example, the comparator 1230 evaluates how close the noise identified by the training network 1220 is to the actual noise added to the patient image. Accuracy or "closeness" of the noise detection can be evaluated by comparison to a tolerance or margin of error such that noticeable noise is left undetected in the image by the network 1220 and no noticeable image data is mistakenly characterized as noise, for example.

At block 1510, if an accurate noise result has been extracted by the training network 1220, then control returns to block 1404 to deploy the training network 1220 as a neural network model 1250 for use with additional patient images. However, if the noise result extracted by the training network 1220 is not accurate enough, then, at block 1512, network weights are adjusted for the training network 1220 based on the noise comparison. Then, the network 1220 can re-evaluate the noisy patient image patches (block 1506) with the updated weight values to determine (at block 1508) whether the adjusted network weights result in more accurate noise determination, for example.

Thus, in an example, after a patient's CT scan data is acquired, a low noise reconstruction is performed (e.g., by smooth kernel, larger pixel size, and/or thicker slice, etc.). The low noise reconstruction image(s) serve as "clean" reference data. Then, the same reconstruction parameters are used with added noise during reconstruction to generate "noisy" reconstruction images. The noise can be added in many ways (e.g., in the projection domain and/or the image domain, etc.). In the projection domain and/or the image domain, the noise can be generated by simulation (e.g., via an analytical calculation, using a Monte Carlo simulation based on noise modellings, etc.) and/or real acquisition (e.g., by repeating scans from any phantoms/animals/cadavers or a single scan from a phantom with uniform regions, etc.). Different phantoms/animals/cadavers may provide different patterns of noise, and phantoms can be either simple phantoms (e.g., water/polyester cylinder/oval or with some inserts, etc.), or anthropomorphic phantoms (e.g., Lungman phantom, Kyoto whole body phantom, etc.), for example. With the "clean" and "noisy" images as training data (e.g., using one or more image transformation models, etc.), a denoising neural network can be trained, such as by using the "noisy" images as input to the network while using "clean" images or "noise" images (calculated by subtracting "clean" image from "noisy" images) as ground truth or comparison images to determine accuracy of network noise detection.

Figure 16:
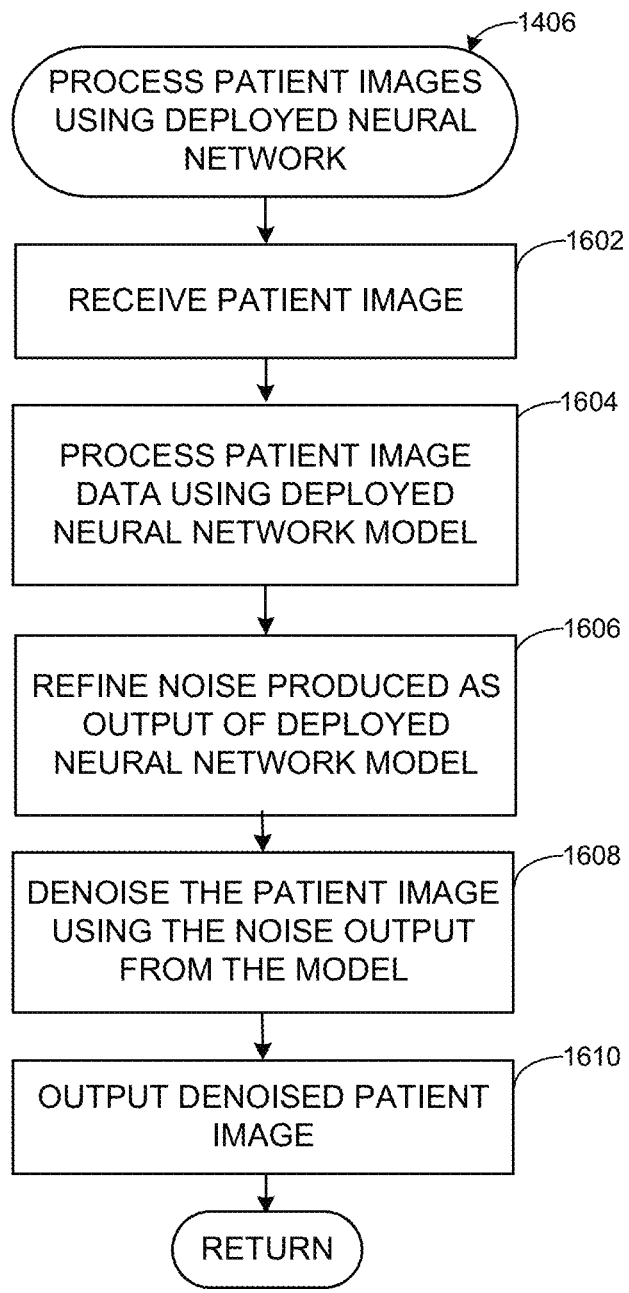

FIG. 16 illustrates an example implementation of processing patient images using the deployed deep neural network model (block 1406) described above with respect to FIG. 14. In this example, at block 1602, patient image data is received. For example, additional thin and/or thick slice images of the patient can be provided from an imaging modality, image archive, electronic medical record, clinical decision support system, radiology reporting/reviewing system, etc.

At block 1604, the patient image data is processed using the deployed deep neural network model 1250 to identify and quantify the noise in the patient image data. For example, the convolutions, filters, etc., using kernels with weights configured during training and set in the deployed model 1250, image features can be distinguished from noise introduced by the imaging scanner and/or other environment/data processing irregularities/errors to identify and quantify noise (e.g., non-image data or artifacts, etc.) present in the patient image data. This indication of noise in the patient image data is output by the deployed model 1250.

At block 1606, noise produced as an output of the deployed neural network model 1250 is refined. For example, the noise can be checked (e.g., based on thresholds, expected values, reference values, etc.) to refine the noise information such as by confirming that image data was not mistakenly included in the noise determination. If image data was mistakenly included, for example, feedback can be generated to re-train the network model 1220 (e.g., after negative feedback exceeds a limit or other threshold) to be redeployed as an updated neural network model 1250, for example.

At block 1608, the patient image data is denoised using the refined noise output from the deployed neural network model 1250. For example, the identified noise values are removed from the patient image data, leaving the actual patient image content without the noise that had been added through the imaging modality and/or other data transmission, processing, storage error, etc.

At block 1610, a denoised patient image is output. For example, one or more denoised patient image slices can be output for display, for storage, for further processing by a clinical decision support system, etc.

Thus, after the network 1220 is trained, the network 1220 can be deployed as a deep neural network model 1250 and used to perform a denoising task on the same patient's image data. For example, a thin slice reconstruction is performed on the same patient scan data with different reconstruction parameters than those used in reconstructing the training images, and the deployed deep learning neural network 1250 is applied to generate a denoised thin slice reconstruction. Any thick (or thin) slice reformat can be generated from the denoised thin slice volume, for example. If the neural network training target was a "clean" image, the output of the deployed model 1250 at inferencing is a denoised image, for example. If the neural network training target was a "noise" image, this "noise" image is subtracted from the "noisy" input to generate a denoised image via the deployed neural network model 1250. Since results in deep learning are not completely predictable, validation checking or refinement is applied to help ensure that the "noise" removed by the deep learning neural network 1250 is indeed noise before subtracting noise from the input image, for example.

While some examples have been shown and described with respect to CT images, the same systems and methods can be applied to MR, x-ray, MICT, ultrasound, etc. In some examples, modalities can be combined such as applying a CT model to MR images, etc.

Figure 17:
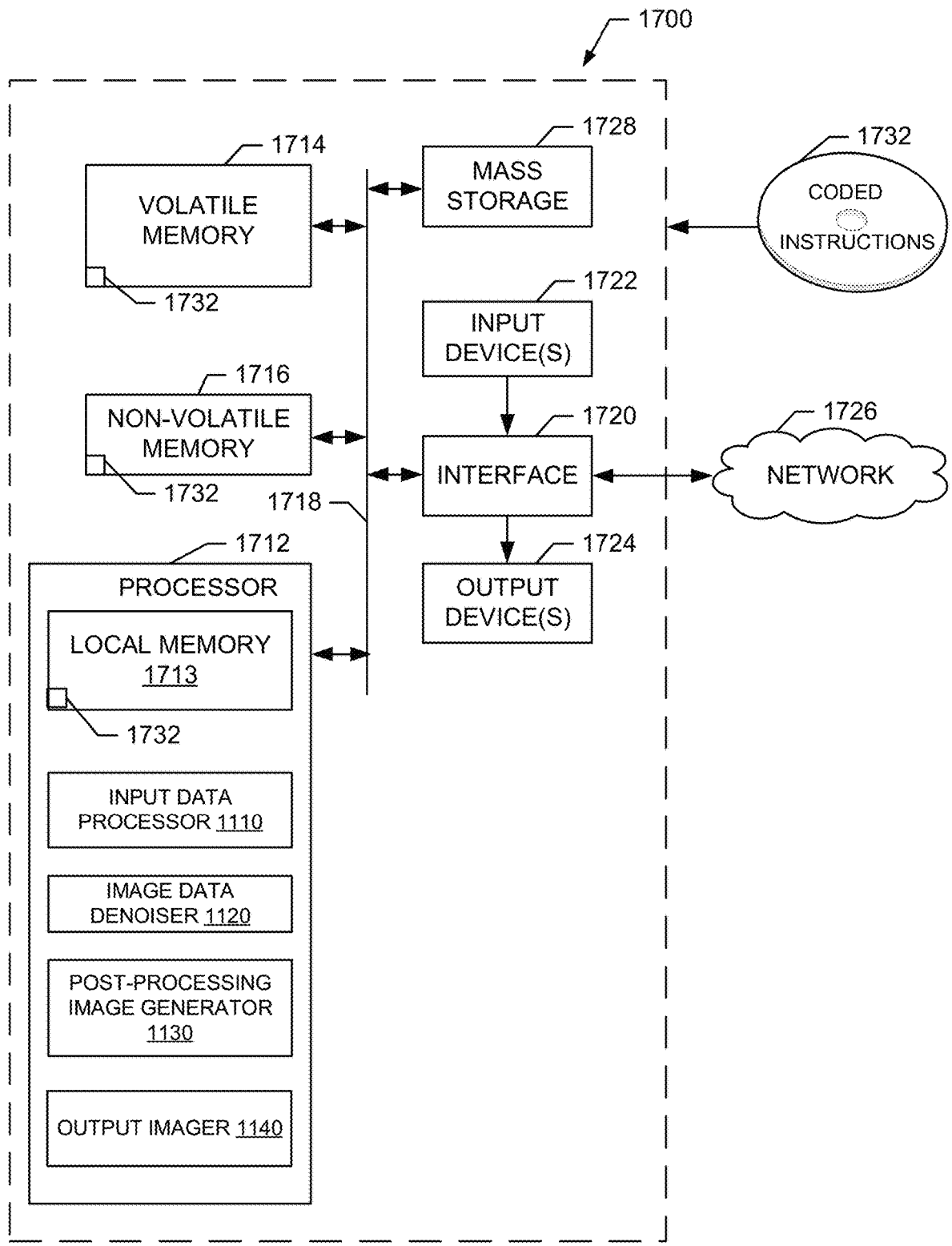
FIG. 17 is a block diagram of a processor platform structured to execute the example machine readable instructions to implement components disclosed and described herein.

FIG. 17 is a block diagram of an example processor platform 1700 structured to executing the instructions of at least FIGS. 14-16 to implement the example components disclosed and described herein. The processor platform 1700 can be, for example, a server, a personal computer, a mobile device (e.g., a cell phone, a smart phone, a tablet such as an iPad™), a personal digital assistant (PDA), an Internet appliance, or any other type of computing device.

The processor platform 1700 of the illustrated example includes a processor 1712. The processor 1712 of the illustrated example is hardware. For example, the processor 1712 can be implemented by integrated circuits, logic circuits, microprocessors or controllers from any desired family or manufacturer.

The processor 1712 of the illustrated example includes a local memory 1713 (e.g., a cache). The example processor 1712 of FIG. 17 executes the instructions of at least FIGS. 14-16 to implement the systems and infrastructure and associated methods of FIGS. 1-13 such as the example input data processor 1110, the example image data denoiser 1120, the example post-processing image generator 1130, the example output imager 1140, or, more generally, the example image processor system 1100, etc. The processor 1712 of the illustrated example is in communication with a main memory including a volatile memory 1714 and a non-volatile memory 1716 via a bus 1718. The volatile memory 1714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1716 may be implemented by flash memory and/or any other desired type of memory device. Access to the main memory 1714, 1716 is controlled by a clock controller.

The processor platform 1700 of the illustrated example also includes an interface circuit 1720. The interface circuit 1720 may be implemented by any type of interface standard, such as an Ethernet interface, a universal serial bus (USB), and/or a PCI express interface.

In the illustrated example, one or more input devices 1722 are connected to the interface circuit 1720. The input device(s) 1722 permit(s) a user to enter data and commands into the processor 1712. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1724 are also connected to the interface circuit 1720 of the illustrated example. The output devices 1724 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1720 of the illustrated example, thus, typically includes a graphics driver card, a graphics driver chip or a graphics driver processor.

The interface circuit 1720 of the illustrated example also includes a communication device such as a transmitter, a receiver, a transceiver, a modem and/or network interface card to facilitate exchange of data with external machines (e.g., computing devices of any kind) via a network 1726 (e.g., an Ethernet connection, a digital subscriber line (DSL), a telephone line, coaxial cable, a cellular telephone system, etc.).

The processor platform 1700 of the illustrated example also includes one or more mass storage devices 1728 for storing software and/or data. Examples of such mass storage devices 1728 include floppy disk drives, hard drive disks, compact disk drives, Blu-ray disk drives, RAID systems, and digital versatile disk (DVD) drives.

The coded instructions 1732 of FIG. 17 may be stored in the mass storage device 1728, in the volatile memory 1714, in the non-volatile memory 1716, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques. The disclosed methods, apparatus and articles of manufacture improve the operation of a computing device by expanding it with a capability to denoise images through incorporation of a deep neural network model trained on a single patient image rather than a large, multi-patient data set. The disclosed methods, apparatus and articles of manufacture are accordingly directed to one or more improvement(s) in the functioning of a computer.

Thus, certain examples provide a computer system and associated method to train and deploy a neural network for denoising and inferencing on a same patient's scan. Using the same patient's scan helps ensure that the deployed deep learning neural network model does not generate anatomical structures that do not belong to the patient during the denoising process.

It is well accepted that the success of deep learning is based on big data, and it is a common belief that more training data leads to a better outcome. However, certain examples using the same patient data to train and inference. It has been demonstrated that by using this patient specific training methodology, one can still achieve the desirable features that deep learning denoising can provide (e.g., nice texture, smooth edges, etc.) while requiring no large data set, no anonymized additional patient data, and/or involvement of other patients beyond the patient in question. Further, certain example provide a great unique advantage in that there is no concern of an anatomical structure (e.g., from another patient) from training data being copied into inferencing data, since the training and inferencing data are from the same patient scan. If another patient's data is used, there is a risk of importing anatomical features from other patients' scans into the current patient scan. If a lesion is copied from training data into a healthy patient, it will cause mis-diagnosis, for example.

Thus, certain examples acquire a patient image, train the network based on the image and added noise, analyze resulting noise identified by the network to ensure that all noise is removed and only noise is removed, and apply the network to subsequent images for that patient. In certain examples, feedback can be used to modify training of the network by scaling the noise added to the patient image used in training. A degree of noise scaling can be based on feedback from reviewed images and associated noise. For a given patient and/or imaging device, if more noise is to be removed, then higher noise can be incorporated into the network training, for example. More or less noise can be introduced into the training patient image via a phantom, for example. Noise can be added to the patient image from a phantom scan, patient scan, computer simulation, etc.

In certain examples, the scaling factor is a fuzzy value (e.g., the factor includes many values (e.g., a range or gradient of values such as all numbers between 0 and 1, rather than a definite integer value), and the noise simulation is also a fuzzy value (e.g., extracted from a phantom scan and/or otherwise simulated, etc.).

In certain examples, the image processor apparatus can be located on the imaging device itself, on a separate computer in communication with the imaging device, on a cloud-based server, etc. The deep learning model-based image denoising can be inserted as part of the image reconstruction chain in conjunction with an imaging device and/or can occur after the image has been obtained and stored in a PACS, for example.

In certain examples, the image processor can expand beyond the single patient's image to train across patients and/or across different imaging devices via the cloud. In certain examples, neural network-based image denoising can be coordinated by a cloud-based server in conjunction with local processors. The cloud server can monitor noise removal remotely, and, if a residual signal from a local processor does not make sense (e.g., does not satisfy certain thresholds, limits, and/or expected values, etc.), the cloud server can trigger an adjustment or modification at the local image processor. Local and/or cloud-based feedback (e.g., from users, from systems using the denoised images, etc.) can be provided to train and/or re-train the neural network model, for example.

In certain examples, an image header (e.g., a DICOM header, etc.) provides information about the image, the patient associated with the image, the imaging device that obtained the image, which reconstruct algorithm to use on the image, etc. An analysis of the DICOM and/or other image file header can be used by the image data denoiser 1120 to train the network 1220 and set parameters for the deployed network model 1250, for example.

In certain examples, a segmentation algorithm expects particular information in a particular format, etc. Thus, the network 1220 is trained differently based on the selected/provided segmentation algorithm. Different algorithms train the network 1220 in different ways. Similarly, different scanners, different patients, and/or different clinicians can train the network 1220 in different ways. For example, a human prefers smoother images for diagnostic viewing, but a machine prefers sharper edges because the processor can denoise the image automatically. The neural network model 1220 can be trained to reflect a particular system with particular properties impacting noise generated by that system, and the model 1220 can then be retrained to look like a different system with different properties to account for noise generated by a different imaging system, for example. Thus, the model 1250 can be dynamically deployed as the network 1220 is retrained with different parameters, for example.

In certain examples, the neural network 1220, 1250 employs a neural style transfer matches local features of a current patient image example with a broader set of examples. Perceptual loss may occur based on image quality. Therefore, a priori training can teach the network 1220 to recognize what makes a good image. Then, the current patient's data can be analyzed to identify low level features, pathology, etc., that satisfies perceptual loss. Perceptual loss is human dependent, so there can be a radiologist-specific perceptual loss, whether the neural network is stored locally or on the cloud. Thus, the network 1250 can be personalized to a personal user's preferences. For example, the training network 1220 can embed characteristics that describe different characteristics, and the network 1220 learns what describes a particular doctor. The network 1220 can then tune how it processes and represents the image for the particular doctor.

In certain examples, personalization can be multi-dimensional. For example, the network model 1250 can be personalized to 1) a particular patient and their associated pathology; 2) a user/reader and their preferences, perception, etc.; 3) an expected pathology (e.g., a pathology-driven kernel learned based on feedback from doctors reviewing for a particular pathology, etc.); etc. Critical-to-quality (CTQ) factors can be accounted for in training 1220 and deploying the neural network model 1250. For example, a blurry image may be acceptable for perfusion but not for facial bones. In certain examples, perceptual loss can be mapped to image quality metrics based on CTQs relevant for a particular target/purpose to help define and/or understand why the network model 1220, 1250 selected a certain perceptual loss as best.

Certain examples take a newly acquired patient image, thicken the image to reduce noise, and then add known noise to the thickened image. In certain examples, a prior patient image can be used instead of or in addition to the current patient image. For example, a contrast image can be used in conjunction with a non-contrast image for the patient; a higher dose exposure can be followed by a low dose exposure (e.g., a chest/lung screen, etc.); etc. For example, an oncology patient may have an initial image at a high dose and a follow-up image at a lower dose. Both images can be used in combination for training of the neural network 1220 for more effective image denoising based on characteristics of that particular patient across multiple images. A multi-modality set of images can allow the neural network 1220 to get better picture of patient, for example.

In certain examples, the neural network 1250 can be used to add noise back into an image. For example, noise can be added to evaluate an affect of scanning at a lower dose. Thus, in reviewing clinical protocols, a protocol may involve scanning at a high dose, and the network 1250 can help evaluate an impact of scanning at a lower dose (and a correspondingly lower resolution with more noise), for example. The network model 1250 can also be used as a simulator for clinical protocol selection and/or control. For example, the CNN can be used to simulate realistic noise, and the real noise used to train the CNN can be used trained to generate real noise patterns that can be used to realistically select an appropriate protocol and dose for the patient, scanner, environment, etc.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An image data processing system comprising:
   a processor; and
   a non-transitory computer readable storage medium in communication with the processor, wherein the processor executes program instructions stored in the computer readable storage medium which cause the processor to:
   process a first patient image of a first patient to add a first noise to the first patient image to form a noisy image input;
   thicken the first patient image from a thin slice image volume to a thick slice image volume to reduce noise in the first patient image before the first noise is to be added to the first patient image;
   process the noisy image input using a first deep learning network to identify the first noise, the image data denoiser to train the first deep learning network using the noisy image input and to modify a network weight based on a comparison of a noise output of the first deep learning network to an expected noise output, wherein, when the first deep learning network is trained to identify the first noise, the image data denoiser is to deploy the first deep learning network as a second deep learning network model to be applied to a second patient image of the first patient to identify a second noise in the second patient image;
   remove the second noise identified by the second deep learning network model from the second patient image to form a denoised patient image; and
   output the denoised patient image.

2. The system of claim 1, wherein the first noise is to be obtained using at least one of a first phantom scan or a simulation.

3. The system of claim 2, wherein the first phantom scan is to be obtained on an imaging scanner used to obtain the first patient image.

4. The system of claim 1, wherein program instructions further cause the processor to:
   scale the first noise based on feedback.

5. The system of claim 1, wherein the identified second noise is to be checked and refined before being removed from the second patient image by the image data denoiser.

6. The system of claim 1, wherein the second deep learning network model is to be deployed with respect to the first patient and wherein the first deep learning network is to be trained with respect to the first patient and a user who is to review the second patient image and diagnose the first patient.

7. A non-transitory computer-readable storage medium including instructions which, when executed, cause at least one processor to at least:
- process a first patient image of a first patient to add a first noise to the first patient image to form a noisy image input;
- thicken the first patient image from a thin slice image volume to a thick slice image volume to reduce noise in the first patient image before the first noise is to be added to the first patient image,
- train the first deep learning network using the noisy image input as input to identify the first noise; and
- when the first deep learning network is trained to identify the first noise, deploy the first deep learning network as a second deep learning network model to be applied to a second patient image of the first patient to identify a second noise in the second patient image, wherein the second noise identified by the second deep learning network model is to be removed from the second patient image to form a denoised patient image to be output.

8. The non-transitory computer-readable storage medium of claim 7, wherein the first noise is to be obtained using at least one of a first phantom scan or a simulation.

9. The non-transitory computer-readable storage medium of claim 8, wherein the first phantom scan is to be obtained on an imaging scanner used to obtain the first patient image.

10. The non-transitory computer-readable storage medium of claim 7, wherein the instructions, when executed, cause the at least one processor to at least scale the first noise based on feedback.

11. The non-transitory computer-readable storage medium of claim 7, wherein the instructions, when executed, cause the at least one processor to at least check and refine the identified second noise before the second noise is removed from the second patient image.

12. The non-transitory computer-readable storage medium of claim 7, wherein the second deep learning network model is to be deployed with respect to the first patient and wherein the first deep learning network is to be trained with respect to the first patient and a user who is to review the second patient image and diagnose the first patient.

13. A computer-implemented method of image denoising comprising:
- processing, using at least one processor, a first patient image of a first patient to add a first noise to the first patient image to form a noisy image input;
- thickening the first patient image from a thin slice image volume to a thick slice image volume to reduce noise in the first patient image before the first noise is to be added to the first patient image,
- training, using the at least one processor, the first deep learning network using the noisy image input as input to identify the first noise; and
- when the first deep learning network is trained to identify the first noise, deploying, using the at least one processor, the first deep learning network as a second deep learning network model to be applied to a second patient image of the first patient to identify a second noise in the second patient image, wherein the second noise identified by the second deep learning network model is to be removed from the second patient image to form a denoised patient image to be output.

14. The method of claim 13, wherein the first noise is to be obtained using at least one of a first phantom scan or a simulation.

15. The method of claim 13, further including scaling the first noise based on feedback.

16. The method of claim 13, further including checking and refining the identified second noise before the second noise is removed from the second patient image.

17. The method of claim 13, wherein the second deep learning network model is to be deployed with respect to the first patient and wherein the first deep learning network is to be trained with respect to the first patient and a user who is to review the second patient image and diagnose the first patient.

* * * * *